United States Patent
Kubisiak et al.

(10) Patent No.: US 6,169,965 B1
(45) Date of Patent: Jan. 2, 2001

(54) FLUID PROPERTY AND FLOW SENSING VIA A COMMON FREQUENCY GENERATOR AND FFT

(75) Inventors: David Kubisiak, Chanhassen; Ulrich Bonne, Hopkins, both of MN (US)

(73) Assignee: Honeywell International Inc., Morristown, NJ (US)

( * ) Notice: Under 35 U.S.C. 154(b), the term of this patent shall be extended for 0 days.

(21) Appl. No.: 09/001,453

(22) Filed: Dec. 31, 1997

(51) Int. Cl.[7] .................. G01N 25/00; G01K 17/06; G06I 15/20
(52) U.S. Cl. .................. 702/136; 702/50; 73/61.76; 374/137; 374/43
(58) Field of Search .................. 702/136, 127, 702/137, 50; 374/43, 40, 44, 137; 73/204.18, 61.76, 54.42; 431/121, 2, 9

(56) References Cited

U.S. PATENT DOCUMENTS

| | | | |
|---|---|---|---|
| 3,015,232 | 1/1962 | Schnoll | 73/204 |
| 3,335,606 | 8/1967 | Scarpa | 73/204 |
| 3,783,356 | 1/1974 | Lide et al. | 318/18 |
| 4,043,196 | 8/1977 | Trageser | 73/204 |
| 4,228,815 | 10/1980 | Juffa et al. | 137/10 |
| 4,279,147 | 7/1981 | Djorup | 73/189 |
| 4,478,076 | 10/1984 | Bohrer | 73/204 |
| 4,483,200 | 11/1984 | Togawa et al. | 73/861.05 |
| 4,507,974 | 4/1985 | Yelderman | 73/861.06 |
| 4,576,050 | 3/1986 | Lambert | 73/861.05 |

(List continued on next page.)

FOREIGN PATENT DOCUMENTS

| | | | |
|---|---|---|---|
| 2934566 | 3/1981 | (DE) | G01P 5/12 |
| 32 34 146 A1 | 3/1984 | (DE) . | |
| 42 22 458 A1 | 1/1994 | (DE) . | |
| 4222458 | 1/1994 | (DE) | G01F 1/68 |
| 4243573 | 6/1994 | (DE) | G01F 1/68 |
| 296 07 315 U | 9/1996 | (DE) | G01P 5/10 |
| 19619133 | 11/1997 | (DE) | G01N 27/18 |
| 0 232 719 | 1/1987 | (EP) . | |
| 0 348 245 A2 | 12/1989 | (EP) . | |
| 0 364 982 A2 | 4/1990 | (EP) . | |

(List continued on next page.)

OTHER PUBLICATIONS

Radiation effects with the AC heated strip technique for the measurement of thermal properties of liquids, S. R. Atalla et al.

Measurement of Thermal Properties of Liquids with an AC Heated–Wire Technique, S.R. Atalla et al, No Date.

Patent Abstracts of Japan, vol. 006, No. 229 (P;–155), Nov. 16, 1982, and JP 57 131029A (Tokyo Shibaura Denki KK), Aug. 13, 1982.

Wolfgang Wehrmann et al.: "Korrelationstechnik" 1980, Expert Verlag, Grafenau XP002094984.

Bonne et al., "Burstproof, Thermal Pressure Sensor for Gases", 1994 Solid State Sensor and Actuator Workshop, 2 pages.

(List continued on next page.)

Primary Examiner—Kamini Shah
(74) Attorney, Agent, or Firm—Ian D. MacKinnon

(57) ABSTRACT

A method and apparatus for using a common frequency generator for measuring selected properties of a fluid of interest via one or more heater and/or sensor elements. The common frequency generator may sequentially and/or simultaneously provide input signals to selected heater and/or sensor elements. Application of more than one frequency component by the common frequency generator enables the determination of one or more time and/or phase lags more efficiently, especially when using an FFT analysis technique. From the time and/or phase lags, the selected fluid properties including fluid flow speed can be determined.

7 Claims, 11 Drawing Sheets

U.S. PATENT DOCUMENTS

| | | |
|---|---|---|
| 4,682,503 | 7/1987 | Higashi et al. .................. 73/755 |
| 4,713,970 | 12/1987 | Lambert .................. 73/861.05 |
| 4,735,082 | 4/1988 | Kolloff .................. 73/27 R |
| 4,909,078 | 3/1990 | Sittler et al. .................. 73/204.26 |
| 4,944,035 | 7/1990 | Aagardl et al. .................. 364/556 |
| 4,961,348 | 10/1990 | Bonne .................. 73/861.02 |
| 5,031,126 | 7/1991 | McCulloch et al. .................. 364/557 |
| 5,044,766 | 9/1991 | Stuart .................. 374/43 |
| 5,056,047 | 10/1991 | Sondergeld .................. 364/556 |
| 5,146,414 | 9/1992 | McKown et al. .................. 364/510 |
| 5,150,611 | 9/1992 | Kleinhans .................. 73/204.14 |
| 5,184,509 | 2/1993 | Kienzle et al. .................. 73/204.14 |
| 5,193,388 | 3/1993 | Kleinhans .................. 73/204.14 |
| 5,237,523 | 8/1993 | Bonne et al. .................. 364/571.03 |
| 5,243,858 | 9/1993 | Erskine et al. .................. 73/204.26 |
| 5,247,156 | 9/1993 | Favre .................. 219/209 |
| 5,263,380 | 11/1993 | Sultan et al. .................. 73/204.26 |
| 5,303,167 | 4/1994 | Bonne .................. 364/556 |
| 5,379,630 | 1/1995 | Lacey .................. 73/25.03 |
| 5,463,899 | 11/1995 | Zemel et al. .................. 73/195 |
| 5,533,412 | 7/1996 | Jerman et al. .................. 73/861.95 |
| 5,587,520 | 12/1996 | Rhodes .................. 73/25.03 |
| 6,019,505 * | 2/2000 | Bonne et al. .................. 374/40 |
| 6,079,253 * | 2/2000 | Bonne et al. .................. 73/61.76 |

FOREIGN PATENT DOCUMENTS

| | | | |
|---|---|---|---|
| 0 419 873 A2 | 8/1990 | (EP) . | |
| 0468 793 A2 | 1/1992 | (EP) . | |
| 0702212 | 3/1996 | (EP) .................. | G01F 1/84 |
| 0702212A | 3/1996 | (EP) . | |
| 0773432 | 5/1997 | (EP) .................. | G01F 1/708 |
| 2287792 | 9/1995 | (GB) .................. | G01P 5/18 |
| 56-153256 | 4/1980 | (JP) .................. | G01P 5/00 |
| 57-131029 | 8/1982 | (JP) .................. | G01K 7/16 |
| 57-206830 | 12/1982 | (JP) . | |
| 9206369 | 4/1992 | (WO) .................. | G01N 27/18 |
| 9206369A | 4/1992 | (WO) . | |
| WO 92/06369 | 4/1992 | (WO) . | |
| WO 94/20825 | 9/1994 | (WO) . | |

OTHER PUBLICATIONS

Lambert et al., "An air flow sensor based on interface thermal wave propagation", *J. Appl. Phys.*, 59(1), Jan. 1986, 3 pages.

Bonne et al., "Natural Gas Flow and Property Sensor", GRI Engine Technology Advisory Committee Meeting, May 1996, 5 pages.

Healy et al., "The Theory of the Transient Hot–Wire Method for Measuring Thermal Conductivity", *Physics*, 82C (1976) pp. 392–408.

Protodyanakonow et al., "The Use of Probes in Investigating Two–Phase Flow", *Fluid Mech., Soviet Res.*, 12, No. 3, (May–Jun. 1983), pp. 98–157.

Carslaw et al., "Conduction of Heat in Solids", $2^{nd}$ Edition, Clarendon Press, Oxford, UK (1959), 7 pages.

Mylroi, "Cross–Correlation Flow Measurement Systems", *G.B.*, 12, No. 6–7, 1977, 4 pages.

Kubisiak et al, "Microamemometer–Based Gas Flow Sensing", IGT Symposium of Natural Gas Quality Measurement, Jul. 1990, 18 pages.

\* cited by examiner

FLUID PROPERTY AND FLOW SENSING VIA A COMMON FREQUENCY GENERATOR AND FFT

CROSS REFERENCE TO CO-PENDING APPLICATIONS

The present application is related to U.S. patent application Ser. No. 09/002,156, filed Dec. 31, 1997, entitled "METHOD AND APPARATUS FOR MEASURING SELECTED PROPERTIES OF A FLUID OF INTEREST USING A SINGLE HEATER ELEMENT", U.S. patent application Ser. No. 09/001,530, filed Dec. 31, 1997, entitled "TIME LAG APPROACH FOR MEASURING THERMAL CONDUCTIVITY AND SPECIFIC HEAT", U.S. patent application Ser. No. 09/002,157, filed Dec. 31, 1997, entitled "TIME LAG APPROACH FOR MEASURING FLUID VELOCITY", and U.S. patent application Ser. No. 09/001,735, filed Dec. 31, 1997, entitled "SELF-OSCILLATING FLUID SENSOR", which are all assigned to the assignee of the present invention and incorporated herein by reference.

BACKGROUND OF THE INVENTION

1. Field of the Invention

The present invention generally relates to the determination of fluid properties and, more particularly, to the determination of the thermal conductivity, thermal diffusivity, specific heat and velocity of a fluid of interest.

2. Description of the Prior Art

A number of approaches have been devised to measure the thermal conductivity, thermal diffusivity, specific heat and fluid velocity of a fluid of interest. Typically, these and other properties are detected through the use of various types of thermal sensors including resistive sensors with thermally isolated drive and sensing elements located on unsupported thin-film bridge or membrane microstructures.

One approach for determining thermal conductivity is described in U.S. Pat. No. 4,735,082 in which a Wheatstone bridge circuit with a heated element in one leg of the bridge is placed or positioned in a cavity and in contact with the sample fluid of interest. The heated element is used to transfer a series of amounts of thermal energy into the fluid of interest at various levels by periodically varying the input voltage to the heater element which, are, in turn, detected at a sensor in another leg as voltage difference signal across the bridge. Integration of the changes of the value of the successive stream of signals yields a signal indicative of the heat dissipation through the fluid, and thus, the thermal conductivity of the fluid.

Further to the measurement of thermally induced changes in electrical resistance, as will be discussed in greater detail below, especially with reference to prior art FIGS. 1–5, very small and very accurate "microbridge" semiconductor chip sensors have been described in which such microelements are used as heaters and sensors. Such sensors might include, for example, a pair of thin film sensor elements around a thin film heater element for measuring flow rates. Semiconductor chip sensors of the class described are treated in a more detailed manner in one or more of patents such as U.S. Pat. No. 4,478,076, U.S. Pat. No. 4,478,077, U.S. Pat. No. 4,501,144, U.S. Pat. No. 4,651,564, and U.S. Pat. No. 4,683,159, all of common assignee with the present invention.

Another approach for measuring the thermal conductivity, thermal diffusivity and specific heat of a fluid is disclosed in U.S. Pat. No. 4,944,035 to Aagard et al. Aagard et al. discloses using a microbridge structure that has a heater film and at least one spaced sensor films. A pulse of electrical energy is applied to the heater at a level and duration such that both a transient change and a substantially steady-state temperature occur at the sensor. The thermal conductivity of the fluid of interest is determined based upon a known relation between the sensor output and the thermal conductivity at steady-state sensor temperatures. The specific heat and thermal diffusivity of the fluid of interest are determined based on a known relation among the thermal conductivity, the rate of change of the sensor output during a transient temperature change in the sensor, and the thermal diffusivity and specific heat.

A typical approach for determining the velocity of a fluid of interest is to determine the time required for a thermal wave to travel from a source heater element to a destination sensor element. By knowing the distance between the heater element and the sensor element, as well as the contribution of thermal diffusivity, the velocity of the fluid can be calculated. This approach is suggested in U.S. Pat. No. 4,576,050 to Lambert. Lambert energizes a heater strip with an oscillating heater input signal to emit thermal waves in the fluid. The thermal waves propagate through the fluid at a rate that is dependent on the fluid velocity that flows perpendicular to the heater strip. A thermo-electric detector, spaced from one or both side of the heater, senses the thermal wave and provides a corresponding detector output signal. The velocity of the fluid is determined, at least to first order, from the time difference between the heater input signal and the detector output signal.

A limitation of many of the above prior art approaches is that a substantial amount of support hardware and/or software are required. For example, in many of the prior art approaches, a number of frequency generators are used to provide a frequency input signal to the heater element. Frequency generators can be relatively expensive, both in terms of hardware and power. Likewise, many of the prior art approaches require one or more high frequency timers to measure the time or phase lag between the heater input signal and a corresponding temperature disturbance in the fluid. Like fixed frequency generators, high frequency timers can be relatively expensive, both in terms of hardware and power. Finally, many of the prior art approaches are prone to errors caused by resistive element drifts.

SUMMARY OF THE INVENTION

The present invention overcomes many of the disadvantages associated with the prior art by providing a fluid sensor that uses a common frequency generator for the heater and/or sensor elements. The frequency generator may sequentially and/or simultaneously provide input signals to selected heater and sensor elements. More than one frequency component may be applied by the common frequency generator to more efficiently obtain time and/or phase lags at various frequencies. Further, it is contemplated that an FFT algorithm may be used to separate the frequency components and/or determine the phase lags of selected input and output signals. From the phase lags, selected fluid properties can be determined as more fully described below. Because the present invention contemplates using phase lags or frequencies to determined the fluid properties, whereby the variability of the involved microheater resistive elements only have a second order influence, the thermal properties of the fluid may be determined more accurately than in many prior art approaches.

In a first illustrative embodiment of the present invention, a frequency generator provides a time-varying input signal to one or both of a heater element and a sensor element. The heater element and the sensor elements are preferably provided in one leg of a corresponding Wheatstone bridge circuit. A heater output signal and a sensor output signal indicate the resistance, and thus the temperature, of the heater element and sensor element, respectively.

Because the heater element is closely coupled to the fluid of interest, the thermal conductivity "k" of the fluid directly affects the time variable temperature response of the heater element. Further, the thermal conductivity of the fluid is typically dependent on the pressure and/or temperature of the fluid. Thus, it has been found that the thermal conductivity, pressure and/or temperature of the fluid of interest can be determined by examining a variable phase lag or time lag between the time-varying input signal provided to the heater element and a subsequent transient temperature response of the heater element when measured with substantially zero fluid flow.

To determine the desired phase lags, the present invention contemplates providing a processor implementing an FFT algorithm. The term processor as used herein includes any hardware or software implementation. The processor may, for example, be used to determining the phase lag between the time-varying input signal and the heater output signal during the transient elevated temperature condition. The processor may receive both the time-varying input signal provided by the frequency generator and the heater output signal. Using an FFT algorithm and/or cross-correlation method, the phase lag between the time-varying input signal and the heater output signal may be determined. From the phase lag, the temperature, pressure and/or thermal conductivity of the fluid of interest can be calculated.

To determine other fluid properties such as thermal diffusivity, specific heat and/or fluid velocity, both the heater and sensor element may be used. In one illustrative embodiment, the frequency generator selectively provides a time-varying input signal to the heater element and the sensor element. Preferably, the frequency generator is first selectively coupled, through a Wheatstone bridge, to the heater element, wherein a heater-to-sensor phase lag is determined using an FFT algorithm. To reduce the effects of the internal phase lag of the sensor element on the transit time, a phase lag between the time-varying input signal provided to the sensor element and the sensor output signal may be determined. In one embodiment, this is accomplished by first uncoupling the frequency generator from the heater element, and then coupling the frequency generator to the sensor element. The processor may then determine the internal phase lag of the sensor element without any interference caused by a temperature disturbance in the fluid provided by the heater element.

The transit time from the heater element to the sensor element may then be determined by subtracting the internal phase lag of the sensor element from the heater-to-sensor phase lag. If the fluid of interest is at substantially zero flow, the thermal diffusivity may then be determined. If the fluid of interest is under flow conditions, the fluid velocity may be determined, after prior calibration.

It is contemplated that a second sensor element may also be provided. Using the approach described above, a second heater-to-sensor phase lag may be determined between the heater element and the second sensor element. Likewise, the internal phase lag of the second sensor element may be determined. By subtracting the internal phase lag of the second sensor element from the corresponding heater-to-sensor phase lag, a second transit time may be determined.

Using the first and second transit times, the fluid velocity can be determined relatively independently of the fluid of interest, without prior calibration.

In another illustrative embodiment of the present invention, the frequency generator may provide two or more fixed frequencies, either sequentially or simultaneously, to the heater element and one or both of the sensor elements. The frequencies are preferably selected to approximate an ideal frequency, wherein the ideal frequency would cause the thermal pulse in the fluid to arrive at the sensor element at the same time the sensor element is energized by the time-varying input signal. The ideal frequency typically depends on a number of factors including the distance between the heater element and the sensor element, selected properties of the fluid, the selected phase lag between heater and sensor inputs, the velocity of the fluid, etc.

The internal phase lag of the sensor element may be determined for each of the fixed frequency components using an FFT algorithm and/or cross-correlation method as described above. The ideal frequency may then be determined by, for example, extrapolating from the internal phase lags at the fixed frequencies to an ideal frequency that would yield an internal phase lag that is equal to the internal phase lag of the sensor element under vacuum conditions. Under vacuum conditions, no heat is transferred from the sensor element to or from the fluid of interest, and thus the temperature of the sensor element would essentially track the temperature of the fluid. A prior calibration procedure may be performed to determine the internal phase lag of the sensor element under vacuum conditions at various frequencies. Once the ideal frequency is identified, the transit time of the temperature disturbance in the fluid can be determined.

It is contemplated that the amplitude of the input signal provided to the sensor element may be adjusted so that the temperature of the sensor element approximates the amplitude of the thermal pulse in the fluid at the sensor element. By compensating for the amplitude of the input signal, the ideal frequency may be more accurately determined.

In another illustrative embodiment of the present invention, the internal phase lags of the heater and/or sensor elements are forced to be negative, while the sensor resistance phase lag versus an input signal provided by a frequency generator is substantially zero. The voltage dependent resistor, preferably a Field Effect Transistor (FET), is preferably provided in one leg of a corresponding Wheatstone Bridge. In this embodiment, the frequency generator provides a time-varying input signal to the voltage dependent resistor. A differential amplifier senses any imbalance in the Wheatstone bridge, and provides the necessary power to balance the Wheatstone bridge via a power input signal. Thus, the resistance and temperature, of the heater and or sensor elements are forced to substantially track the resistance of the voltage dependent resistance, or in this case, the time-varying input signal. Accordingly, the phase lags between the heater and/or sensor elements and the time-varying input signal are forced by the differential amplifier to be substantially zero.

The transit time for the temperature disturbance to travel from the heater element to the sensor element can be detected by sensing the phase shift of the power input signal provided by the differential amplifier to balance the Wheatstone bridge of the sensor. In a preferred embodiment, two or more frequencies are provided by the frequency generator to the heater and sensor elements. A processor implementing an FFT algorithm may then determine the phase shift of the power input signals provided to the Wheatstone Bridge of the sensor element for each of the frequency components. An ideal frequency can then be determined by, for example, extrapolating from the measured phase shifts in the power input signal to a phase shift that corresponds to an ideal condition.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention, then, is directed to a system that determines selected fluid properties including thermal conductivity, specific heat, thermal diffusivity and velocity of a fluid of interest using a common frequency generator for the heater and/or sensor elements. Further, it is contemplated that an FFT analysis may be used to separate various frequency components, when provided, and/or determine the desired phase lags between selected signals.

The preferred embodiments of the present invention contemplate holding a microscopic sized heating element in a sample of the fluid of interest. The micromembrane or microsensor system or "microbridge", as it will be referred to herein, though not limiting, is presently preferred for several reasons. The system is extremely fast reacting, is very accurate, very sensitive because of its advantageous coupling to the fluid of interest and small and adaptable to a variety of configurations.

The microbridge semiconductor chip sensor contemplated, for example, in certain embodiments preferred for the invention may resemble the form of one or more of the microbridge systems illustrated in U.S. Pat. No. 4,478,076, U.S. Pat. No. 4,478,077, U.S. Pat. No. 4,501,144, U.S. Pat. No. 4,651,564, U.S. Pat. No. 4,683,159, and U.S. Pat. No. 4,994,035, all of common assignee with the present invention.

Figure 1:
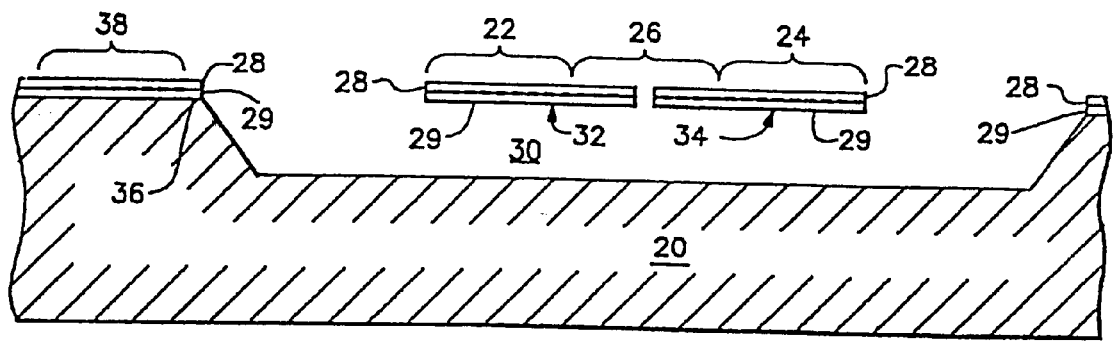
FIGS. 1, 2 and 3 are different views of a prior art embodiment of a microbridge flow sensor.
Figure 2:
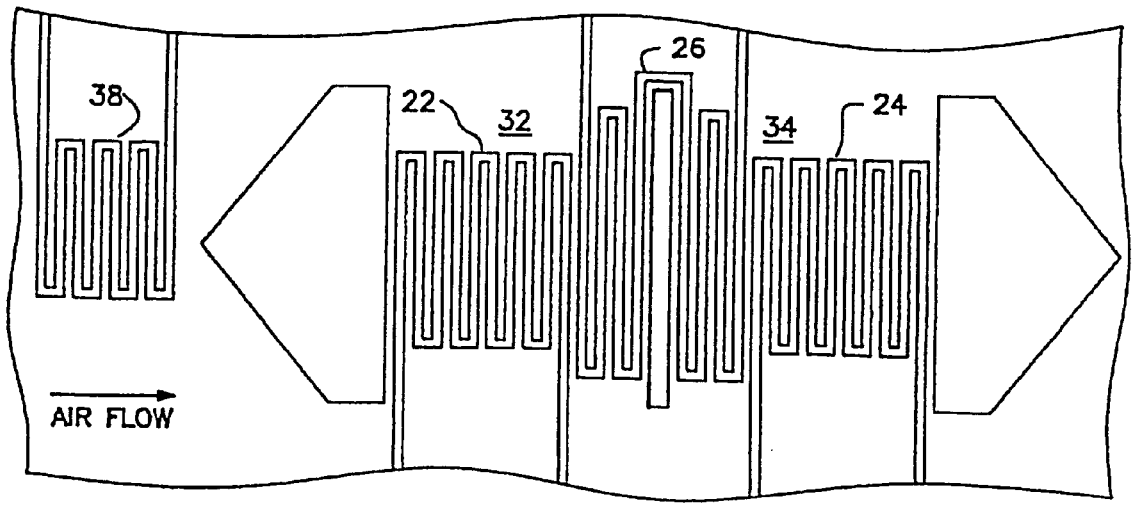
Figure 3:
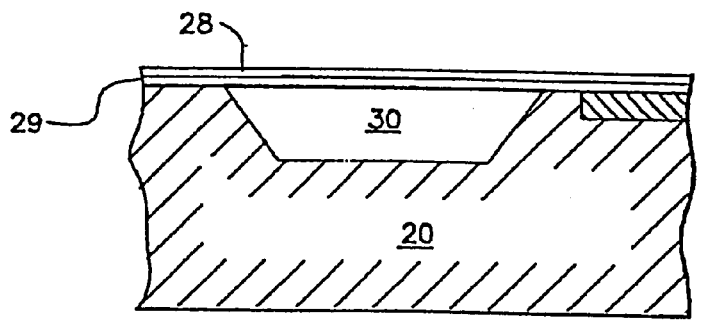

Such a system is exemplified by FIGS. 1–3 taken from U.S. Pat. No. 4,994,035 to Aagard et al. A discussion of that example will now be presented as it will be helpful in understanding the present invention. While the present discussion is believed sufficient, to the extent necessary, any additional material contained in the microbridge related patents cited is deemed to be incorporated herein by reference.

The prior art system of FIGS. 1–3 contemplates a pair of thin film temperature sensors 22 and 24, a thin film heater 26 and a support member 20 supporting the sensors and heater out of contact with the base substrate. Sensors 22 and 24 are shown disposed on opposite sides of heater 26. Support member 20 is a non-conductive isolating or semiconductive material. A silicon was chosen here because of its adaptability to precision etching techniques and ease of electronic chip producibility. The embodiment includes two identical temperature sensing resistor grids 22 and 24 acting as the thin film heat sensors and a centrally located heater resistor grid 26 acting as the thin film heater.

Sensors 22 and 24 and heater 26 may be fabricated of any suitable, stable metal or alloy film. The metal used may be a platinum or nickel-iron alloy, also referred to as permalloy, with a composition of 80 percent nickel and 20 percent iron. The sensor and heater grids are encapsulated in a thin film of dielectric, typically comprising layers 28 and 29 and preferably silicon nitride, $Si_3N_4$ to form the film members. Other thin film materials may include $SiO_2$, MgO, SiC, $Al_2O_3$, etc.

In FIGS. 1 and 2, the sensor comprises two thin film members 32 and 34, with member 32 comprising sensor 22 and member 34 comprising sensor 24, each member comprising one-half of heater 26 and having a preferred dimension of 150 microns wide and 400 microns long. The heater 26 may, however, may be as small as 10 microns wide and 30 microns long.

The system further describes an accurately defined fluid space (liquid or gas) 30 that effectively surrounds elements 22, 24, 26, and is achieved by fabricating the structure on silicon surface 36. Thin film elements 22, 24 and 26 have thicknesses of approximately 0.08 to 0.12 micron with line widths on the order to 5 microns and spaces between lines on the order of 5 microns. The elements encapsulated in the silicon nitride film preferably have a total thickness of approximately 0.8 microns or less. The fluid space 30 may be fabricated by subsequently etching an accurately defined silicon-free depression of about 100 microns deep into silicon body 20 beneath members 32 and 34.

Members 32 and 34 connect to top surface 36 of semiconductor body 20 at one or more edges of etched-pit or depression 30. As illustrated in FIG. 3, members 32 and 34 may be bridged across depression 30; alternately, for example, members 32 and 34 could be cantilevered over depression 30, or be part of a continuous top membrane surface, formed after etching the silicon away from the back.

In the system shown, heat flows from the heater to the sensor by means of both solid and fluid couplings therebetween. Of note is the fact that silicon nitride ($Si_3N_4$), besides being a good electrical insulator, is an effective solid thermal insulator. Because of the effective thermal insulation, heat transmission through the solid silicon nitride within members 32 and 34 does not dominate the propagation of heat from heater 26. This further enables a relatively high amount of the heat conducted to sensing resistors 22 and 24 from heater resistor 26 to be by transmission through the surrounding fluid rather than through the supporting nitride film. Moreover, the supporting silicon nitride film has a low enough thermal conductivity that sensing resistor grids 22 and 24 can be located immediately adjacent or juxtaposed to heating resistor grid 26. Thus, sensing resistor grids 22 and 24 are in effect suspended rigidly in the fluid space proximate heater resistor 26 and act as thermal probes to measure the temperature of the fluid near and in the plane of heater resistor grid 26.

Figure 4:
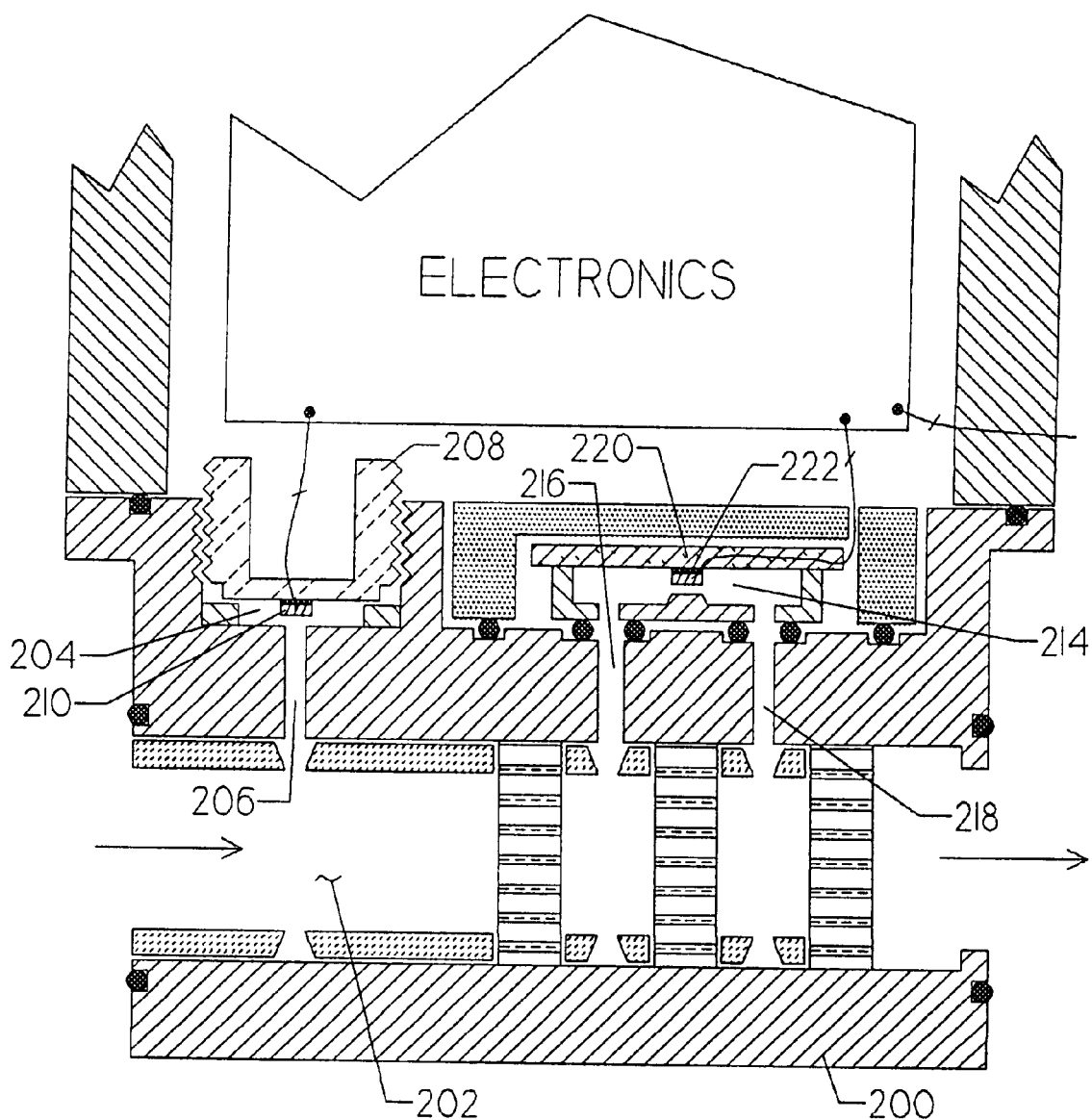
FIG. 4 is a partial cut-away view of a fluid property and flow sensor system based on thermal microbridge or micromembrane sensors.

FIG. 4 is a partial cut-away view of a flow sensor system based on thermal microsensors placed in line with a flow pipe. A main flow channel 200 having a central bore 202 is connected to the pipe that carries most of the fluid of interest. A first chamber 204 is in fluid communication with the central bore 202 of the main flow channel 200 via a single bore 206. A header 208 having a first microbridge or micromembrane sensor 210 mounted thereto is inserted into the first chamber 204 and secured to the main flow channel 200 as shown. In this configuration, the first microbridge sensor is exposed to some fraction of the fluid of interest with substantially zero flow. The first microbridge sensor 210 is typically used to measure fluid properties such as thermal conductivity, thermal diffusivity, specific heat, temperature and pressure.

A second sensor 222 is positioned in a bypass channel 214. In this configuration, the second microbridge sensor 222 is exposed to the flow of the fluid of interest. The second microbridge sensor 222 is typically used to measure fluid velocity.

Figure 5:
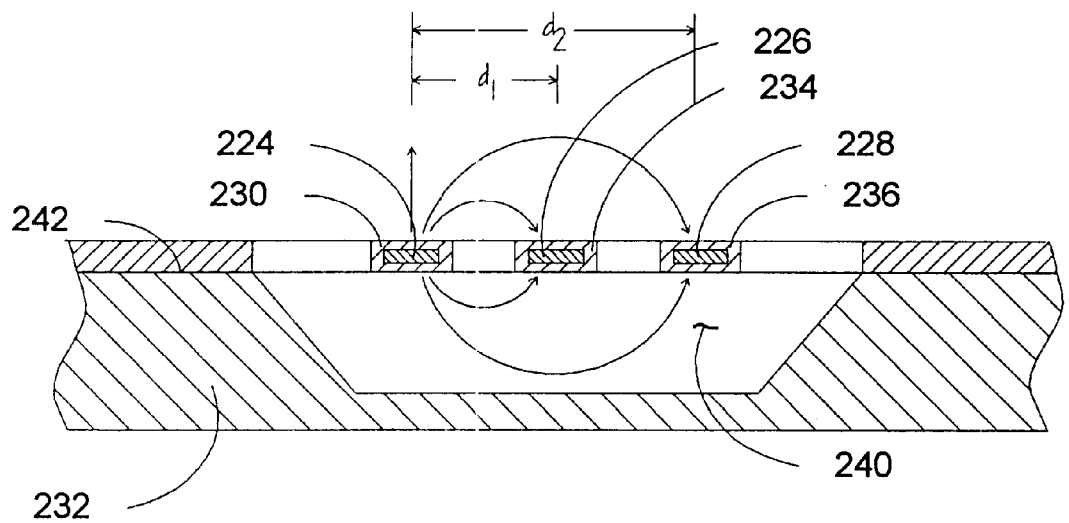
FIG. 5 is a first illustrative cross sectional view of a microbridge sensor in accordance with the present invention having two downstream sensor elements.

FIG. 5 is a first illustrative cross sectional view of a microbridge sensor having two downstream sensor elements. When using calibration data to measure the thermal conductivity, thermal diffusivity, specific heat and/or velocity of a fluid of interest, only one heater element, or one heater element and one sensor element may be required. However, as discussed in more detail below, some embodiments of the present invention include a heater element 224 and at least two spaced sensor elements 226 and 228. For example, when measuring fluid velocity, at least two sensor elements 226 and 228 may be provided, each preferably spaced a different distance from the heater element 224. In the illustrative diagram, sensor 226 is spaced a first distance "$d_1$" from the heater element 224, and sensor 228 is spaced a second distance "$d_2$" from the heater element 224. Both sensor 226 and 228 are shown downstream from the heater element 224.

The heater element 224 is shown having a support member 228 that supports the heater element 230 out of contact with the base substrate 232. Together, the heater element 224 and support member 230 form a heater film member. Likewise, the sensor element 226 is shown having a support member 234 that supports the sensor element 226 out of contact with the base substrate 230. Together, the sensor element 226 and support member 234 form a first sensor film member. Finally, the sensor element 228 is shown having a support member 236 that supports the sensor element 228 out of contact with the base substrate 230. Together, the sensor element 228 and support member 236 form a second sensor film member.

Heater element 224 and sensor elements 226 and 228 may be fabricated of any suitable, stable metal or alloy such as platinum, nickel, iron—nickel, etc. Heater element 224 and sensor elements 226 and 228 may be any resistive element including a wire, but are preferably a film. Moreover, heater element 224 and sensor elements 226 and 228 may be of any shape including a grid pattern as described above, or simply a line. As indicated above, the heater element 224 and sensor elements 226 and 228 are preferably encapsulated in a thin film of dielectric, such as $Si_3N_4$, $SiO_2$, MgO, SiC, $Al_2O_3$, to form the support members 230, 234 and 236.

An accurately defined fluid space 240 is preferably provided which effectively surrounds heater element 224 and sensor elements 226 and 228, and is achieved by fabricating the structure on silicon surface 242. Heater element 224 and sensor elements 226 and 228 preferably have thicknesses of approximately 0.08 to 0.12 micron, with line widths on the order to 5 microns and, if a grid is used, spaces between lines on the order of 5 microns. The fluid space 240 may be fabricated by subsequently etching an accurately defined depression about 100 microns deep into silicon substrate 232 beneath heater element 224 and sensor elements 226 and 228. Another method may include forming a membrane structure by etching the silicon out from the back of the silicon substrate 232.

Support member 230 and heater element 224 preferably connect to top surface 242 of semiconductor substrate 232 at one or more edges of etched-pit or depression 240. Support member 230 and heater element 224 may bridge across depression 240 as shown, or alternately, for example, may be cantilevered over depression 240. The sensor elements 234 226 and 228 are preferably similarly constructed. It is recognized that any number of heater and sensor elements may be provided in a like manner. However, for illustration purposes, only one heater element 224 and two sensor elements 226 and 228 are shown in FIG. 5.

The heater element 224 produces a thermal disturbance in the fluid. Each of the sensor elements 226 and 228 may sense the arrival of the thermal disturbance at their respective locations. Of interest is the transit times for the temperature disturbance to travel from the heater element 224 to each of the sensor elements 226 and 228. As described more fully below, because the sensor elements 226 and 228 are spaced at different distances from the heater element, the fluid velocity can be determined relatively independently of the fluid properties, especially if the spacings are large compared to the diffusion-governed displacements.

Figure 6:
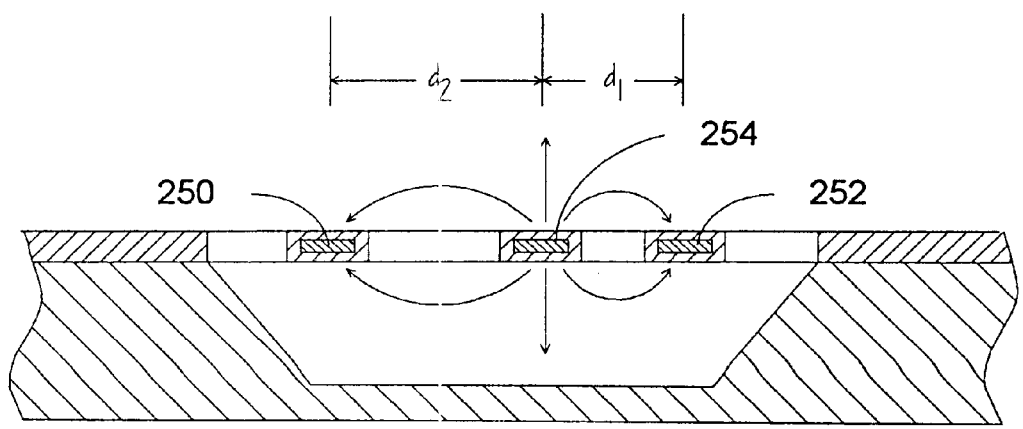
FIG. 6 is a second illustrative cross sectional view of a microbridge sensor in accordance with the present invention having an upstream and a downstream sensor element.

Rather than providing both sensors downstream from the heater element as shown in FIG. 5, it is contemplated that one sensor element 250 may be placed upstream and another sensor 252 may be placed downstream of the heater element 254, as shown in FIG. 6.

Figure 7:
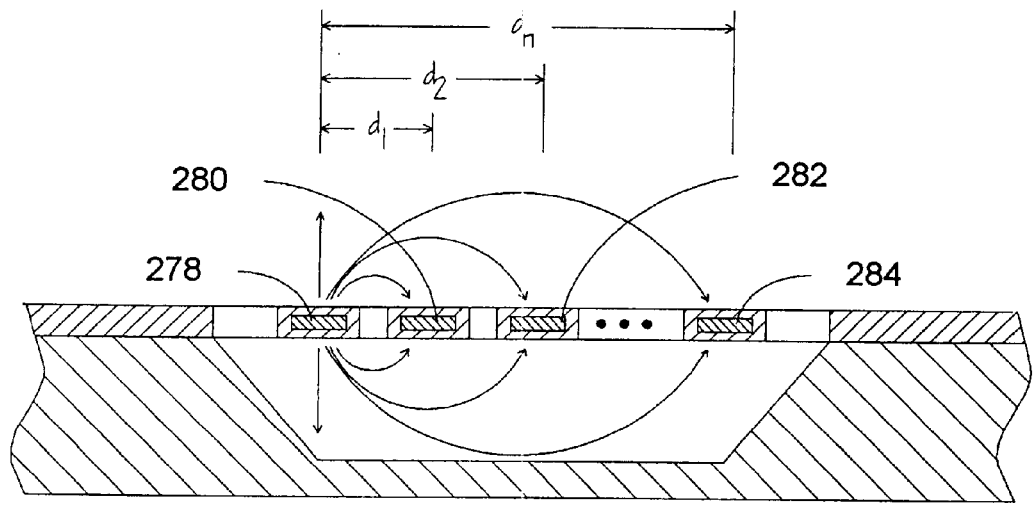
FIG. 7 is a third illustrative cross sectional view of a microbridge sensor in accordance with the present invention having more than two downstream sensor elements.

Again referring to selected fluid velocity measurements, and to reduce the possible negative effects of thermal diffusivity and other properties of the fluid at low flow rates, it is contemplated that a first set of sensor elements may be used for measuring low flow rates and another set may be used for higher flow rates. For example, in FIG. 7, those sensor that are positioned closest to the heater element, such as sensor elements 280 and 282, may be used to measure low flow rates, as the thermal diffusivity component may be negligible even at the low flow rates at the appropriate amplitude and frequency. Likewise, sensor elements that are positioned further from the heater element may be used to measure the higher flow rates, including sensor 284. Using this approach, the effect of the thermal diffusivity component on the flow rate measurement may be minimized.

In addition, it is contemplated that a higher amplitude heater input signal may be provided when measuring high flow rates, and conversely, a lower amplitude heater input signal may be provided when measuring low flow rates. A higher amplitude temperature disturbance can be more easily detected, but can increases the speed of the thermal diffusivity component in the fluid. Thus, a lower amplitude heater input signal may reduce the speed of the thermal diffusivity component, and provide more accurate results at lower flow rates.

Figure 8:
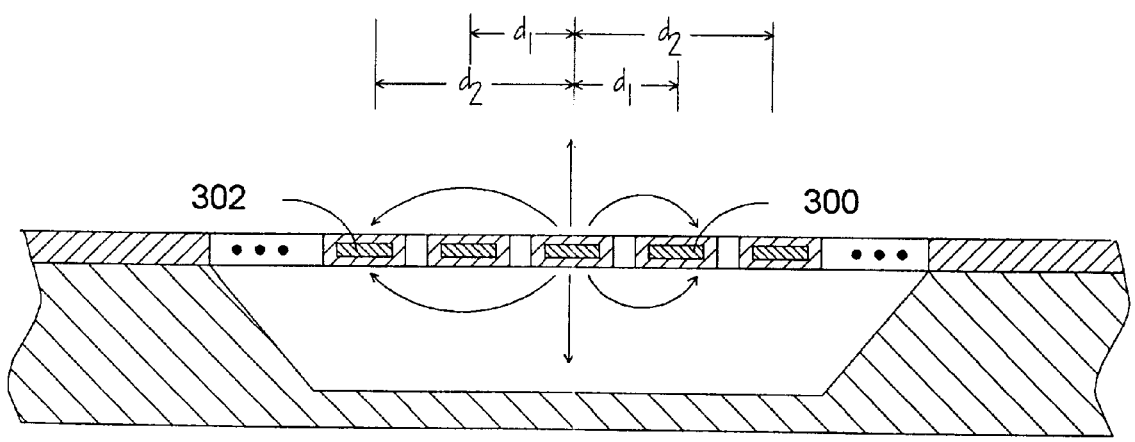
FIG. 8 is a fourth illustrative cross sectional view of a microbridge sensor in accordance with the present invention having a number of downstream and upstream sensor elements.

FIG. 8 is a fourth illustrative cross sectional view of a microbridge sensor in accordance with the present invention having a number of downstream and upstream sensor elements. In this embodiment, several pairs of sensor elements are equally spaced from the heater element both in an upstream and downstream direction. When using calibration data to measure the thermal conductivity, thermal diffusivity, specific heat and/or fluid velocity of a fluid of interest, only one heater element and one sensor element may be required. However, as discussed in more detail below, some embodiments of the present invention include a heater element and at least two spaced sensor elements 300 and 302. When measuring fluid velocity, for example, using at least two spaced sensor elements 300 and 302, only the outputs of selected sensor elements that are spaced at different distances from the heater element may be selected. This may allow the fluid velocity to be obtained relatively independently of the other fluid properties, as discussed in more detail below.

Figure 9:
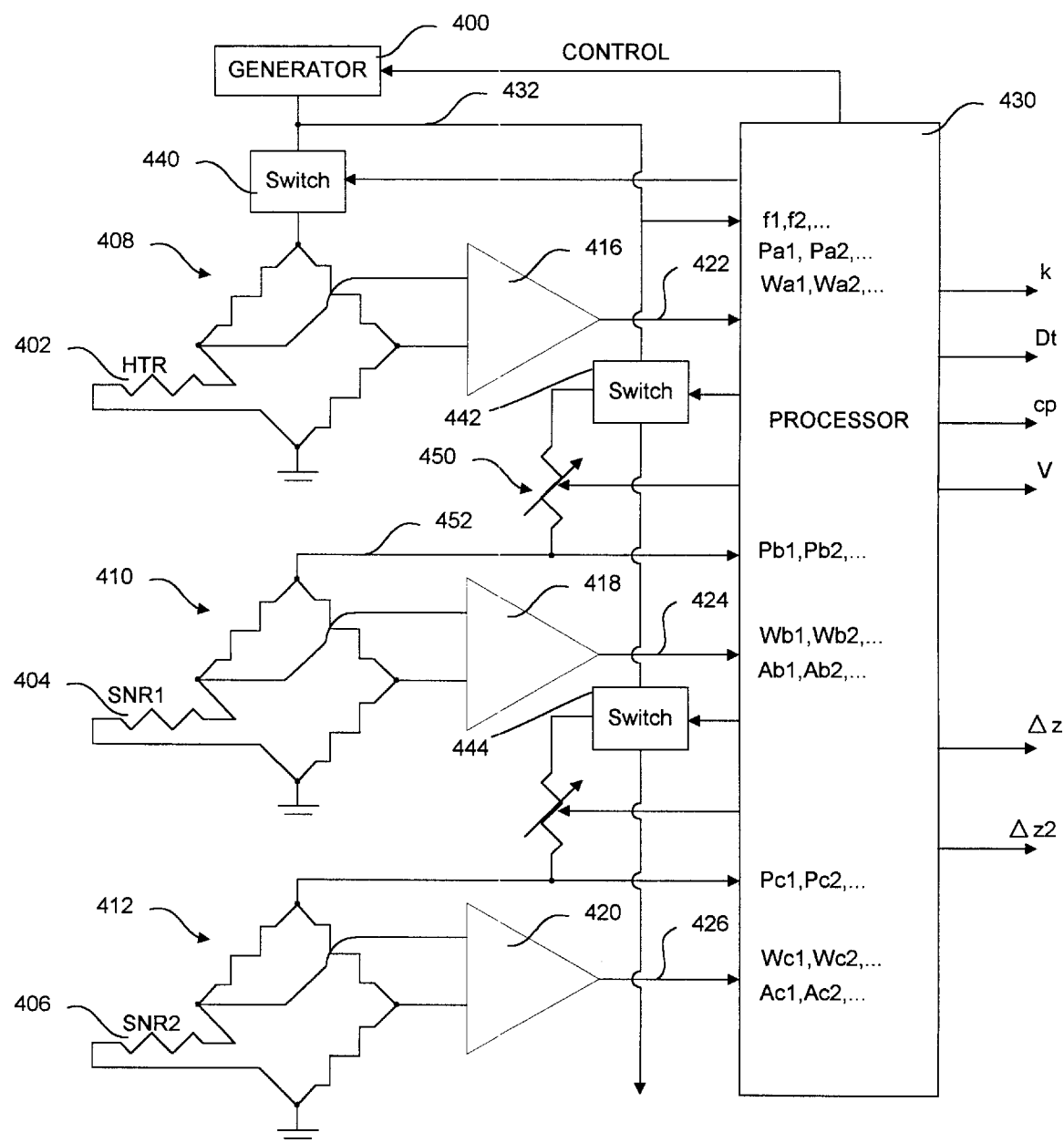
FIG. 9 is a schematic diagram of a first illustrative embodiment of the present invention.

FIG. 9 is a schematic diagram of a first illustrative embodiment of the present invention. A common frequency generator 400 provides a time-varying input signal to a heater element 402, a first sensor element 404 and a second sensor element 406 via Wheatstone Bride circuits 408, 410 and 412, respectively. Differential amplifiers 416, 418 and 420 provide a heater output signal 422, a first sensor output signal 424 and a second sensor output signal 426, respectively. The output signals are representative of the resistance, and thus the temperature, of the corresponding element.

A processor 430 receives the time-varying input signal provided by the frequency generator 400, along with the heater output signal 422, the first sensor output signal 424 and the second sensor output signal 426. In a preferred embodiment, processor 430 determines selected phase lags between these signals using an FFT and/or cross-correlation analysis, as more fully described below.

To determine the thermal conductivity, pressure and/or temperature of a fluid of interest, it is contemplated that only the heater element 402 need be used. Because the heater element 402 is closely coupled to the fluid of interest, the thermal conductivity, k, of the fluid directly affects the time variable temperature response of the heater element 402. Further, the thermal conductivity of the fluid is typically dependent on the pressure and/or temperature of the fluid. Thus, it has been found that the thermal conductivity, pressure and/or temperature of the fluid of interest can be determined by examining a variable phase lag or time lag between the time-varying input signal provided to the heater element 402 and a subsequent transient temperature response of the heater element 402 when measured with substantially zero fluid flow.

To determine the variable phase lag or time lag between the time-varying input signal 432 and the heater output signal 422, it is contemplated that processor 430 may use a known FFT analysis and/or cross-correlation method. Using an FFT analysis and/or cross-correlation method, the phase lag between the time-varying input signal 432 and the heater output signal 422 may be determined. For example, the thermal conductivity, k, of the fluid of interest can be calculated from the phase lag, γ, using the relation, $$k=\{-2\pi f c_{pv} t/\tan(\gamma)-h_3\}L_1 \quad (1)$$

where, $c_{pv}$=the specific heat per unit volume for the heater film and support member (10% platinum, 90% $Si_3N_4$ microbridge composite, $J/(cm^3 k)$;

t=the heater film thickness, cm $h_3$=the coefficient of conductive heat transfer to the substrate, $W/cm^3$; and $L_1$=the characteristic length of thermal conduction from the heater element into the fluid phase, cm.

The derivation of equation (1), and a further discussion thereof, can be found on the above-referenced U.S. patent application Ser. No. 09/002,156, filed Dec. 31, 1997, entitled "METHOD AND APPARATUS FOR MEASURING SELECTED PROPERTIES OF A FLUID OF INTEREST USING A SINGLE HEATER ELEMENT", which has been incorporated herein by reference.

To determine other fluid properties such as thermal diffusivity, specific heat and/or fluid velocity, the heater element 402 and one sensor element 404 may be used. Preferably, the frequency generator 400 is first selectively coupled, through Wheatstone bridge 408, to the heater element 402. This causes a temperature disturbance in the fluid of interest, which can be detected by the sensor element 404. Thus, processor 430 can determine a heater-to-sensor phase lag between heater element 402 and sensor element 404, preferably using an FFT analysis and/or cross-correlation method.

To reduce the effects of the internal phase lag of the sensor element 404 on the transit time, the frequency generator 400 may be uncoupled from the heater element, via switch 440, and then coupled to the sensor element 404 via switch 442. An internal phase lag between the time-varying input signal provided to the sensor element 404 and the sensor output signal 424 may then be determined without interference from a temperature disturbance in the fluid caused by the heater element 402.

A first transit time 425 from the heater element 402 to the sensor element 404 may then be determined by subtracting the internal phase lag of the sensor element 404 from the heater-to-sensor phase lag. If the fluid of interest is under flow conditions, the fluid velocity may be determined from the first transit time 425, after prior calibration. If the fluid of interest is at substantially zero flow, the thermal diffusivity, $D_t$, may then be determined using the relation:

$$D_t = d^2/4\Delta z \quad (2)$$

where,
- d=the effective distance between said heater element 402 and the sensor element 404; and
- Δz=the transit time between the heater element 402 to the sensor element 404 at substantially zero flow.

The volumetric specific heat, $c_{pv}$, of the fluid of interest may then be determined using the relation $$c_{pv}=k/D_t \qquad (3)$$

where,
- k=the thermal conductivity of the fluid of interest,
- $D_t$=the thermal diffusivity determined above.

The derivation of equations (2) and (3), and a further discussion thereof, can be found on the above-referenced U.S. patent application Ser. No. 09/001,530, filed Dec. 31, 1997, entitled "TIME LAG APPROACH FOR MEASURING THERMAL CONDUCTIVITY AND SPECIFIC HEAT", which has been incorporated herein by reference.

Accordingly, an illustrative method for determining a selected property of a fluid of interest may include the steps of: providing a time-varying input signal; coupling the input signal to the heater element; sensing the temperature change in the fluid of interest at a spaced location via the sensor element; determining a heater-to-sensor phase lag for the temperature change in the fluid to travel from the heater element to the sensor element; decoupling the input signal from the heater element; coupling the input signal to the sensor element, the input signal causing a temperature change in the sensor element; determining a sensor phase lag between the input signal and the corresponding temperature change in the sensor element; subtracting the sensor phase lag from the heater-to-sensor phase lag to provide a transit phase lag; and determining the selected property of the fluid of interest using the transit phase lag.

It is contemplated that a second sensor element 406 may also be provided. Using the approach described above, a second heater-to-sensor phase lag may be determined between the heater element 402 and the second sensor element 406. Likewise, the internal phase lag of the second sensor element 406 may be determined. By subtracting the internal phase lag of the second sensor element 406 from the corresponding heater-to-sensor phase lag, a second transit time 427 may be determined. Using the first and second transit times, the fluid velocity can be determined relatively independently of the fluid of interest, without prior calibration, using the relation:

$$v=\{(d_1^2/\Delta z_1 - d_2^2/\Delta z_2)/(\Delta z_1 - \Delta z_2)\}^{0.5} \qquad (4)$$

where,
- $d_1$=the distance between the heater element 402 and the first sensor element 404;
- $d_2$=the distance between the heater element 402 and the second sensor element, where $|d_1| \neq |d_2|$;
- $\Delta z_1$=the first time lag value; and
- $\Delta z_2$=the second time lag value.

The derivation of equation (4), and a further discussion thereof, can be found on the above-referenced U.S. patent application Ser. No. 09/002,157, filed Dec. 3, 1997, entitled "TIME LAG APPROACH FOR MEASURING FLUID VELOCITY", which has been incorporated herein by reference.

Thus, an illustrative method for determining the velocity of a fluid of interest may include the steps of: providing a time-varying input signal; coupling the input signal to a heater element; sensing the temperature change in the fluid of interest at a first spaced location via a first sensor element; determining a first heater-to-sensor phase lag for the temperature change in the fluid to travel from the heater element to the first sensor element; sensing the temperature change in the fluid of interest at a second spaced location via a second sensor element; determining a second heater-to-sensor phase lag for the temperature change in the fluid to travel from the heater element to the second sensor element; decoupling the input signal from the heater element; coupling the input signal to the first sensor element; determining a first sensor phase lag between the input signal and the corresponding temperature change in the first sensor element; subtracting the first sensor phase lag from the first heater-to-sensor phase lag to provide a first transit phase lag; coupling the input signal to the second sensor element, the input signal causing a temperature change in the second sensor element; determining a second sensor phase lag between the input signal and the corresponding temperature change in the second sensor element; subtracting the second sensor phase lag from the second heater-to-sensor phase lag to provide a second transit phase lag; and determining the velocity of the fluid of interest using the first transit phase lag and the second transit phase lag.

In another illustrative embodiment of the present invention, the frequency generator may provide two or more fixed frequencies, either sequentially or simultaneously, to the heater element 402 and one or both of the sensor elements 404 and 406. When providing the frequencies simultaneously, switches 440, 442 and 444 are preferably set to provide the time-varying input signal 432 to the corresponding heater and sensor elements.

Figure 10:
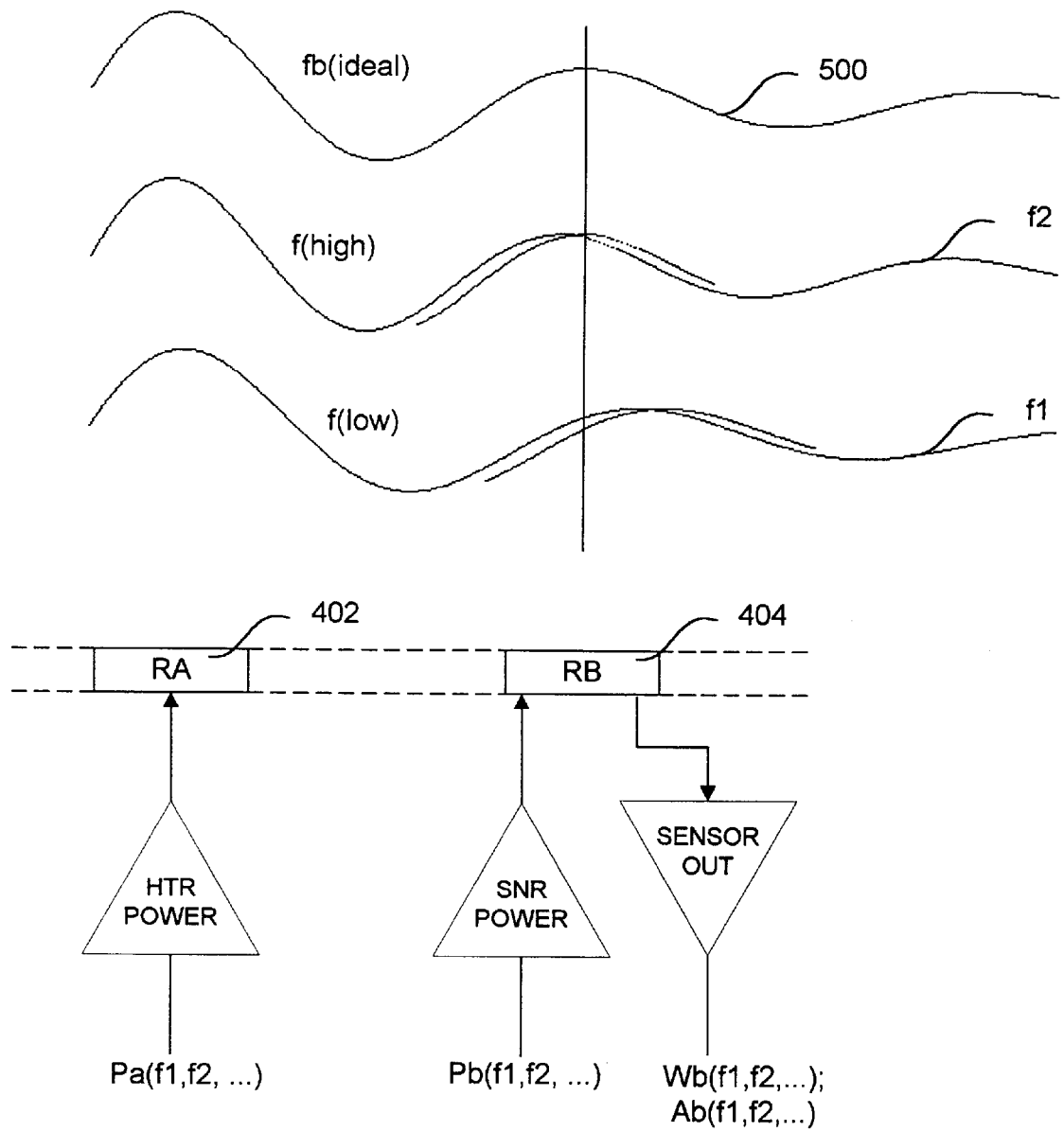
FIG. 10 is a diagram showing an ideal frequency for a heater/sensor combination and two fixed frequencies provided by the frequency generator of FIG. 9.

The fixed frequencies are preferably selected to approximate an ideal frequency. An ideal frequency is defined as the frequency that causes the temperature disturbance in the fluid to arrive at, for example, sensor element 404 at the same time that sensor element 404 is energized by the time-varying input signal. Referring to FIG. 10, an ideal frequency is shown at 500, and peaks at both the heater element 402 and the first sensor element 404. As is apparent, the ideal frequency typically depends on a number of factors including the distance between the heater element 402 and the sensor element 404, selected properties of the fluid, the selected phase lag between heater and sensor inputs, the velocity of the fluid, etc.

The amplitude of the input signal provided to the sensor element 404 may be adjusted using resistor 450 so that the temperature of the sensor element 404 approximates the amplitude of the temperature disturbance in the fluid. In an ideal case, the frequency and amplitude of the input signal 452 provided to the sensor element 404 causes the internal phase lag of the sensor element to match the internal phase lag of the sensor element under vacuum conditions. Under a vacuum condition, no heat is transferred from the sensor element to or from the fluid of interest, and thus the temperature of the sensor element 404 essentially tracks the temperature of the fluid. Once the ideal frequency is identified, the transit time of the temperature disturbance in the fluid can be determined.

To determine the ideal frequency, it is contemplated that two or more fixed frequencies may be provided to both the heater element 402 and, for example, sensor element 404. The internal phase lag of the sensor element 404 for each of the frequency components is then determined by processor 430 using, for example, an FFT analysis and/or cross-correlation method as described above. The ideal frequency may then be determined by, for example, extrapolating from the internal phase lags at the fixed frequencies to an ideal frequency that would yield an internal phase lag that is equal to the internal phase lag of the sensor element 404 under vacuum conditions. The internal phase lag of the sensor elements 404 and 406 under vacuum conditions may be determined during a calibration procedure. During the calibration procedure, sensor elements 404 and 406 may be exposed to a vacuum condition, and the internal phase lags thereof may be determined by processor 430.

Figure 11:
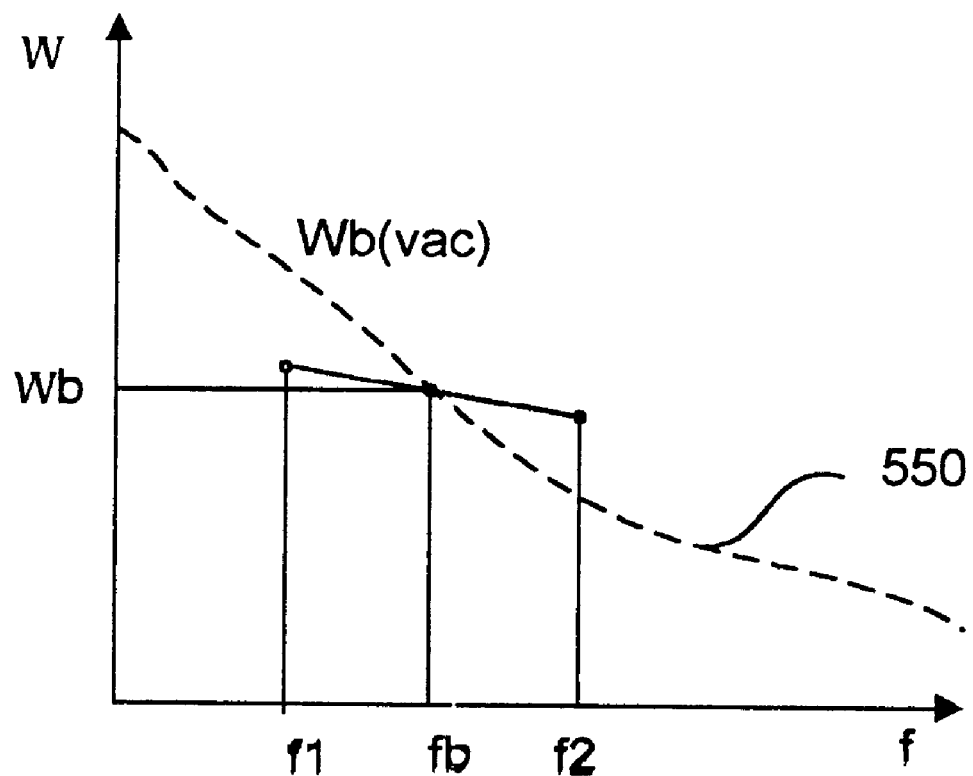
FIG. 11 is a graph showing an illustrative method for determining an ideal frequency from the measured internal phase lags of the sensor element at two fixed frequencies.

Referring specifically to FIG. 11, a curve 550 is shown representing the internal phase lag of the first sensor element 404 under vacuum conditions versus frequency. Preferably one of the fixed frequency components (f1) provided by the frequency generator 400 (see FIGS. 9–10) is selected to be lower than the expected ideal frequency (fb). Likewise, one of the fixed frequency components (f2) provided by the frequency generator 400 is selected to be higher than the expected ideal frequency (fb). The ideal frequency (fb) may then be determined by interpolating between the internal phase lags at the fixed frequencies to determine the frequency that crosses curve 550. This frequency represents the ideal frequency for the heater-sensor pair. From the ideal frequency, the transit time from the heater element to the sensor element can be calculated, as described above.

The thermal conductivity and specific heat may be calculated using the transit time when the fluid is at substantially zero flow. Likewise, the velocity of the fluid can be determined from the transit time, if prior calibration has been performed.

Figure 12:
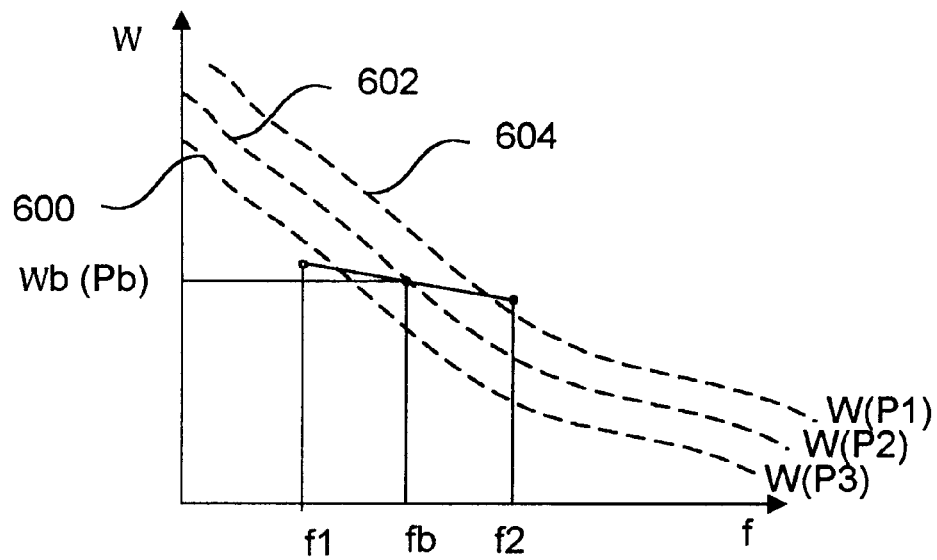
FIG. 12 is a graph showing an illustrative method for determining an ideal frequency from the measured internal phase lags of the sensor element at two fixed frequencies using the ideal power amplitude graph of FIG. 13.

It is recognized that the amplitude of the input signal may affect the internal phase lag of the sensor element, including under vacuum conditions. For example, in FIG. 12, a number of phase lag curves 600–604 are shown under vacuum conditions, each corresponding to a different amplitude input signal. Thus, to more accurately determine the ideal frequency for the first sensor element 406, it may be desirable to account for the amplitude of the input signal 452.

Figure 13:
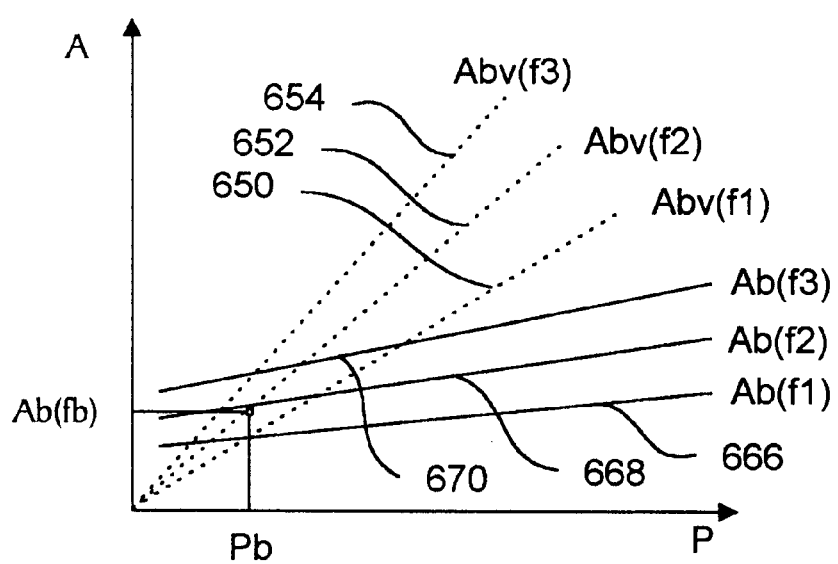
FIG. 13 is a graph showing an illustrative method for determining an ideal power amplitude for the time-varying input signal that is provided to the sensor element.

FIG. 13 shows three curves 650, 652 and 654 representing the temperature response of the sensor element 406 versus the amplitude of the input signal 452 under vacuum conditions at three frequencies f1, f2 and f3. Also shown are three curves 666, 668, and 670 representing the temperature response of the sensor element 406 versus the amplitude of the input signal 452 under non-vacuum conditions at the same three frequencies F1, F2 and F3. The ideal amplitude of the input signal 452 corresponds to the intersection of an amplitude curve under non-vacuum conditions and an amplitude curve under vacuum conditions, at the ideal frequency Fb (see FIG. 12). The ideal amplitude for the input signal may be used to determine the ideal frequency Fb, as discussed above with reference to FIG. 12. Since there are two unknowns, namely the ideal frequency (Fb) and the ideal amplitude of the input signal (Pb), and two sets of curves, namely those shown in FIG. 12 and 13, the ideal frequency (Fb) and the ideal amplitude of the input signal (Pb) may be determined using conventional methods, assuming that for small enough changes in A and P, the problem can be solved with linear equations.

Referring back to FIG. 9, it is contemplated that a second transit time from the heater element 402 and the second sensor element 406 may determined in a similar manner. Using both the first and second transit times, the velocity of the fluid of interest may be determined, relatively independent of the properties of the fluid, using the relation of equation (4).

Accordingly, an illustrative method for determining a selected property of a fluid of interest may include the steps of: energizing a heater element and a first sensor element with at least two time-varying input signals, each having a different frequency; sensing the resistance change of the first sensor element; determining a lag between selected ones of the at least two time-varying input signals and the corresponding resistance change of the first sensor element; and determining a first ideal input frequency that would produce a phase lag between an ideal time-varying input signal and the resistance change of the first sensor element that substantially equals a first calibrated phase lag value.

A method for providing calibration phase lag data for the first sensor element may include the step of: subjecting the first sensor element to a vacuum condition; energizing the first sensor element with one or more first sensor input signals, each having a different frequency; and determining a number of first calibrated phase lag values between the first sensor input signals and the corresponding resistance change of the first sensor element. Similar methods may be used for a second sensor element.

Figure 14:
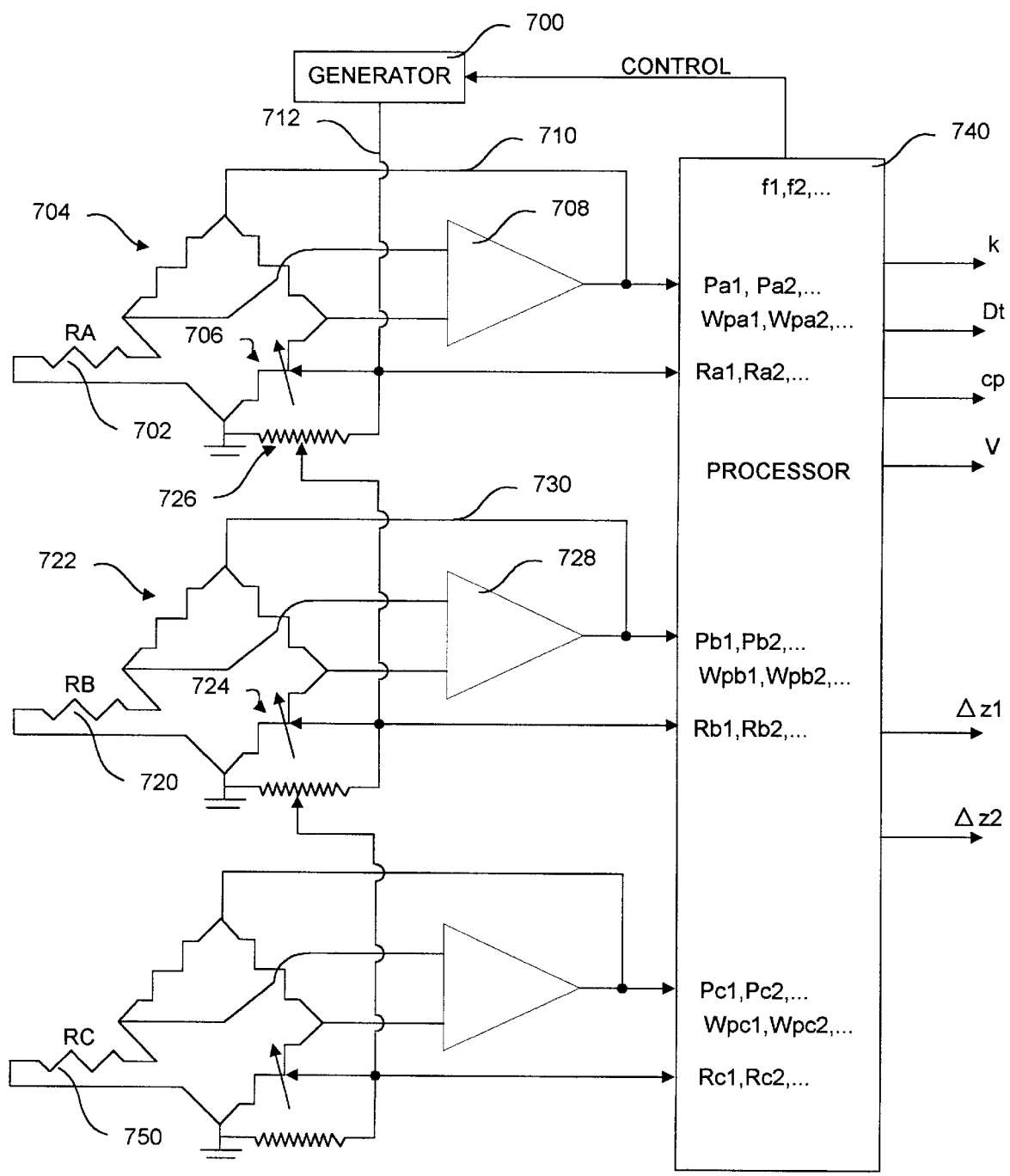
FIG. 14 is a schematic diagram of a second illustrative embodiment of the present invention wherein the internal phase lags of the heater and sensor elements are forces to substantially zero.

Another illustrative embodiment of the present invention is shown in FIG. 14. In this embodiment, the internal phase lags of the heater and/or sensor elements are forced to substantially zero, and the transit time from the heater element to a sensor element is determined from a phase lag in the power signal provided to the respective sensor elements.

Referring specifically to FIG. 14, a heater element 702 is included in one leg of a modified Wheatstone bridge 704. The modified Wheatstone bridge includes a voltage dependent resistor 706 in the leg opposite the heater element 702, which is controlled by a time-varying input signal 712 provided by frequency generator 700. A differential amplifier 708 senses any imbalance in the Wheatstone bridge 704, and provides the necessary power to balance the Wheatstone bridge 704 via a power input signal 710. In this configuration, the resistance and therefore the temperature of the heater element 702 is forced to substantially track the resistance of the of the voltage dependent resistor 706, or in this case, the time-varying input signal 712. By definition, then, the phase lag between the temperature of the heater element 702 and the time-varying input signal is forced to be substantially zero.

To determine the thermal conductivity of the fluid of interest, processor 740 may determine the phase shift in the power input signal 710 relative to a predetermined reference or calibration function, such as equation (1). Processor 740 may then relate the phase shift in the power input signal 710 to the thermal conductivity of the fluid of interest.

To determine the thermal diffusivity, specific heat and velocity of a fluid of interest, a first sensor element 720 may be included in one leg of a second modified Wheatstone bridge 722. The second Wheatstone bridge 722 includes a voltage dependent resistor 724 in the leg opposite the first sensor element 720, which is controlled by the time-varying input signal. The amplitude of the time-varying input signal is preferably reduced by resistor 726 before it is provided to the voltage dependent resistor 724 of the second modified Wheatstone bridge 722 so that the temperature of the first sensor element 720 substantially tracks the temperature disturbance in the fluid. The amount that the amplitude is reduced may be determined by prior calibration.

Like above, a differential amplifier 728 senses any imbalance in the second Wheatstone bridge 722, and provides the necessary power to balance the bridge 722 via a power input signal 730. In this configuration, the resistance and temperature of the first sensor element 720 is forced to substantially track the resistance of the voltage dependent resistor 724, or in this case, the time-varying input signal 712 having a reduced amplitude. By definition, then, the phase lag between the temperature of the first sensor element 720 and the time-varying input signal provided by the frequency generator is forced to be substantially zero. The transit time for a temperature disturbance to travel from the heater element 702 to the first sensor element 720 is determined from the phase shift of the power input signal 730, as further described below.

Figure 16:
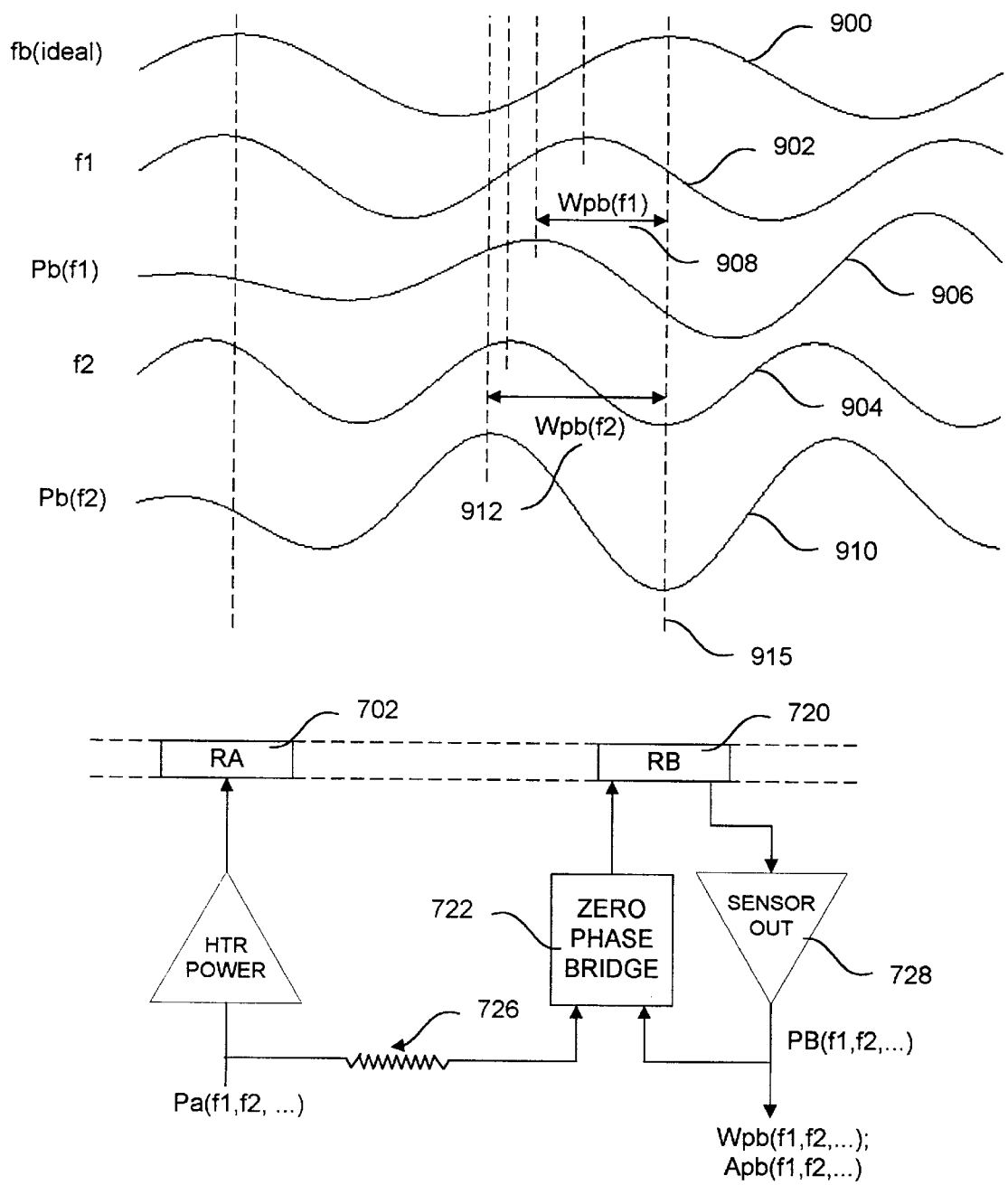
FIG. 16 is a diagram showing an ideal frequency for a heater/sensor combination, two fixed frequencies provided by the frequency generator of FIG. 14, and the resulting phase shift of the power input signals provided by the differential amplifier of the sensor circuitry.

In a preferred embodiment, two or more fixed frequencies are provided by frequency generator 700 to the heater element 702 and the first sensor element 720. The fixed frequencies are preferably selected to approximate an ideal frequency. The ideal frequency is defined as the frequency that causes the temperature disturbance in the fluid to arrive at, for example, sensor element 720 at the same time that sensor element 720 is energized. This is explicitly shown in FIG. 16. The ideal frequency is shown at 900 which peaks at both the heater element 702 and the first sensor element 720. The ideal frequency typically depends on a number of factors including the distance between the heater element 702 and the sensor element 720, selected properties of the fluid, the selected phase lag between heater and sensor inputs, the velocity of the fluid, etc.

A first fixed frequency component, "f1", is sown at 902, and a second fixed frequency component, "f2", is shown at 904. The first fixed frequency component causes the differential amplifier 728 to provide a first power input signal to the zero phase Wheatstone bridge 722. The first power input signal is shown at 906. Likewise, the second fixed frequency component causes the differential amplifier 728 to provide a second power input signal to the zero phase Wheatstone bridge 722. The second power input signal is shown at 910.

Processor 740 preferably implements an FFT analysis, provides and determines the phase shift of the power input signal 730 provided to the second modified Wheatstone Bridge 722 for each of the frequency components. For example, a first phase shift for the first power input signal 906 is shown at 908, and a second phase shift for the second power input signal 910 is shown at 912. For the illustrative embodiment, an arbitrary reference 915 has been chosen. An ideal frequency is then preferably determined by, for example, interpolating between the measured phase shifts in the power input signal 730 at the two or more input frequencies, to an ideal phase shift that corresponds to the ideal frequency 900. This frequency is ideal because it meets the requirements described below. The ideal phase shift may be determined by prior calibration. As described above, a first transit time may be calculated from the ideal frequency, and selected properties of the fluid of interest can be determined from the first transit time including thermal diffusivity (provided the fluid velocity is known or negligible) and fluid velocity.

The amplitude of the fixed frequency input signals may be adjusted using resistor 726 so that the temperature of the sensor element 720 approximates the amplitude of the temperature disturbance in the fluid. In an ideal case, the frequency and amplitude of the input signal cause the sensor element 720 to essentially track the temperature disturbance in the fluid.

A second sensor element 750 may also be provided. Using the second sensor element 750, a second ideal frequency may be determined. From the second ideal frequency, a second transit time may be determined. Using the first and second transit times, the velocity of the fluid of interest may be determined, relatively independent of the properties of the fluid, using equation (4) as described above.

Figure 15:
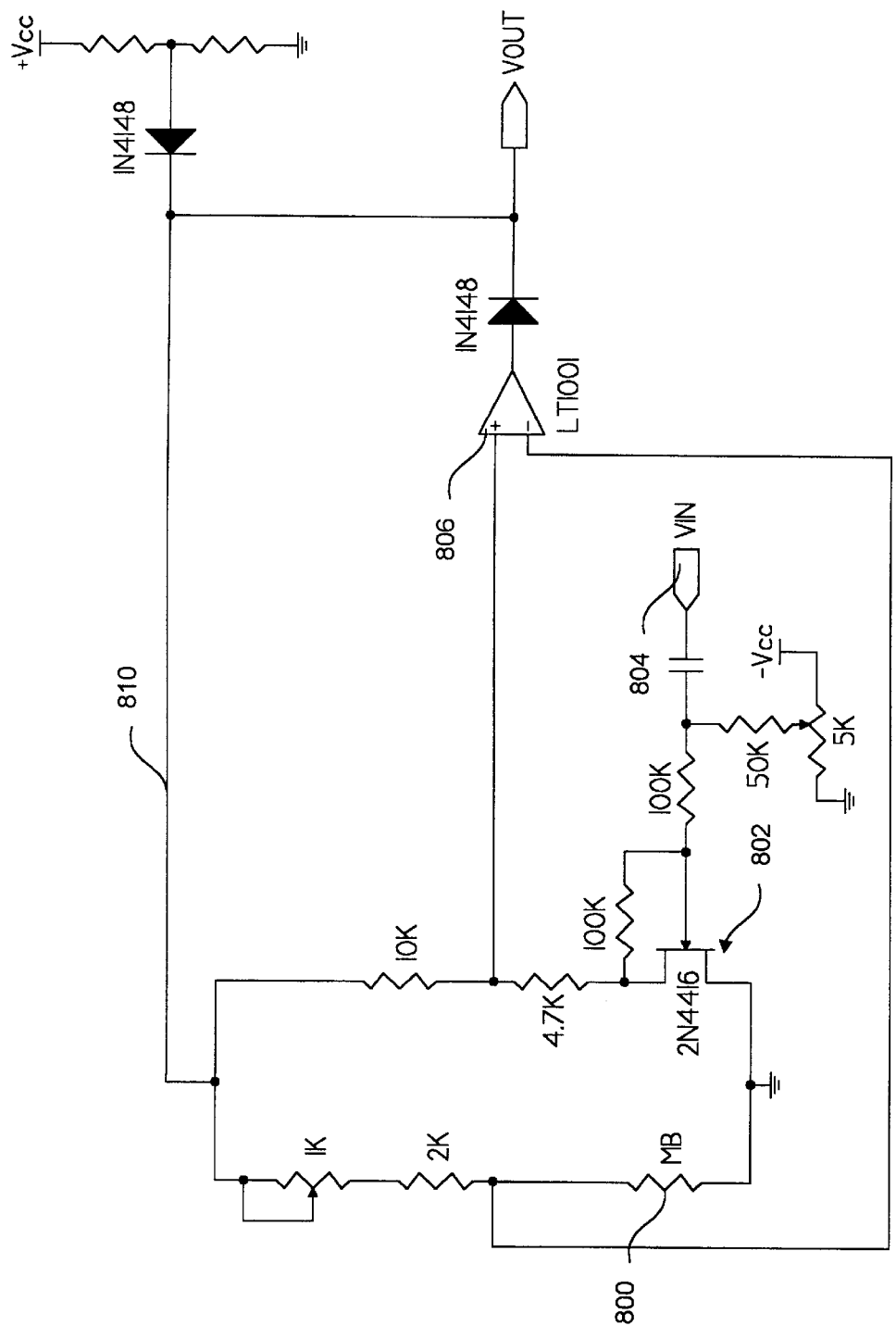
FIG. 15 is a more detailed schematic diagram of one of the Wheatstone bridge and amplifier circuits of FIG. 14.

FIG. 15 is a more detailed schematic diagram of one of the Wheatstone bridge and amplifier circuits of FIG. 14. The Wheatstone bridge circuit of FIG. 15 includes a microbridge (heater or sensor) element 800 in one leg and a voltage dependent resistor 802 in an opposite leg. The voltage dependent resistor 802 is preferably a Field Effect Transistor (FET), and is controlled by a time-varying input signal provided to a $V_{in}$ port 804. Both sides of the Wheatstone bridge are coupled to a differential amplifier 806 as shown. The differential amplifier 806 senses any imbalance in the Wheatstone bridge, and provides the necessary power to balance the bridge via a power input signal 810. In this configuration, the resistance and therefore the temperature of the microbridge element 800 are forced to substantially track the resistance of the of the voltage dependent resistor 802, or in this case, the time-varying input signal provide to the VIN port 804.

Having thus described the preferred embodiments of the present invention, those of skill in the art will readily appreciate that the teachings found herein may be applied to yet other embodiments within the scope of the claims hereto attached.

What is claimed is:

1. Apparatus for determining a selected property of a fluid of interest, comprising:

heater means in thermal communication with the fluid of interest, said heater means having a resistance that changes with temperature;

energizing means connected to said heater means for energizing said heater means, said energizing means providing a periodic time-varying input signal to said heater means to induce a transient elevated temperature condition in said heater means;

output means for providing an output signal that is related to the resistance of said heater means;

FFT means for determining a phase lag between the input signal and the output signal during the transient elevated temperature condition using an FFT analysis; and determining means for determining the selected property of the fluid of interest using the phase lag.

2. Apparatus according to claim 1 wherein the FFT analysis includes a cross-correlation analysis for cross-correlating the input signal and the output signal during the transient elevated temperature condition to determine the phase lag therebetween.

3. Apparatus according to claim 1 wherein said periodic time-varying input signal comprises two or more frequency components, and said FFT means determines a phase lag for each of the two or more frequency components.

4. Apparatus according to claim 1 wherein said selected property is selected from the group consisting of temperature, pressure and thermal conductivity.

5. A method for determining a selected property of a fluid of interest using a heater element, wherein the heater element has a resistance that changes with temperature and is in thermal communication with the fluid of interest, the method comprising the step of:

providing a time-varying input signal to the heater element, the input signal causing a temperature change, and a corresponding resistance change, in the heater element;

sensing the resistance change of the heater element;

determining a phase lag between the input signal and the sensed resistance change of the heater element using an FFT analysis; and determining the selected property of the fluid of interest using the phase lag.

6. A method according to claim 5 wherein said periodic time-varying input signal comprises two or more frequency components, and a phase lag is determined for each of the two or more frequency components.

7. A method according to claim 5 wherein said selected property is selected from the group consisting of temperature, pressure and thermal conductivity.

* * * * *